United States Patent
Sivavec et al.

(10) Patent No.: US 6,436,710 B1
(45) Date of Patent: Aug. 20, 2002

(54) HEADSPACE SAMPLING AND MONITORING SYSTEMS AND METHODS

(75) Inventors: Timothy Mark Sivavec, Clifton Park; Sunita Singh Baghel; Don Royall Houston, both of Rensselaer; Angelo Anthony Bracco, Albany, all of NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/556,287

(22) Filed: Apr. 24, 2000

(51) Int. Cl.7 .................................................. G01N 1/18
(52) U.S. Cl. .................. 436/39; 73/19.1; 73/23.41; 95/8; 95/241; 96/101; 96/202; 96/218; 422/68.1; 436/177; 436/181
(58) Field of Search ............................ 210/85, 87, 188, 210/916; 436/39, 161, 177, 180, 181; 422/50, 68.1, 99, 101, 102; 73/19.1, 23.2, 23.41, 23.42, 61.56, 61.59, 863.81, 863.85, 864.21, 864.25, 864.81, 864.83; 96/155, 156, 202, 218

(56) References Cited

U.S. PATENT DOCUMENTS

| | | | | |
|---|---|---|---|---|
| 5,127,259 A | * | 7/1992 | Kahl et al. | 73/19.1 |
| 5,222,032 A | * | 6/1993 | Fleming | 73/19.1 |
| 5,258,057 A | * | 11/1993 | Baykut | |
| 5,266,496 A | * | 11/1993 | Dacruz | 73/19.1 |
| 5,363,707 A | * | 11/1994 | Augenblick et al. | 73/864.81 |
| 5,693,538 A | * | 12/1997 | Capuano et al. | 436/181 |
| 5,792,423 A | * | 8/1998 | Markelov | 73/864.21 |
| 6,146,895 A | * | 11/2000 | Green et al. | 436/177 |

FOREIGN PATENT DOCUMENTS

| | | |
|---|---|---|
| DE | 39 00 799 | 6/1990 |
| DE | 40 07 064 | 9/1991 |
| JP | 2000 028617 | 1/2000 |

OTHER PUBLICATIONS

W. Burgeois and RM Stuetz, "Measuring Wastewater Quality Using a Sensor Array: Prospects for Real Time Monitoring", Water Science and Technology, vol. 41, No. 12, pp. 107–112, 2000, XP002174565.

(List continued on next page.)

Primary Examiner—Joseph W. Drodge
(74) Attorney, Agent, or Firm—Toan P. Vo; Noreen C. Johnson (57) ABSTRACT

A headspace sampling system monitors materials in wastewater. The headspace sampling system comprises a sample receptacle that can contain a wastewater sample; a sparger chamber vapor column; a sample receptacle cover assembly that connects the sparger chamber vapor column to the sample receptacle; a sparger tube; at least one sensing device; and at least one analytic device. The sparger tube and the sample receptacle define a headspace. The sparger chamber vapor column is in communication with the sample receptacle and is closed by a sparger chamber vapor column cover at a second end that is opposed to the sample receptacle. The sparger tube extends into the sample receptacle and the wastewater sample in the sample receptacle. The sparger tube is connected to a source of inert gas at a first end opposed to the sample receptacle and comprises a dispersion device at an end opposed to the first end. The sensing device is disposed in the headspace sampling system in the headspace. The analytic device in communication with the least one sensing device. Inert gas can flow through the sparger tube into the wastewater sample to separate materials from the wastewater, the sparged materials entering the headspace of the headspace sampling system. The sparged materials are sensed by the sensing device thus providing material signal characteristics, which can be analyzed by the analytic device to determine characteristics of the material from the material signal characteristics and provide information about the characteristics of the material.

41 Claims, 3 Drawing Sheets

OTHER PUBLICATIONS

JG Converse et al., "Static headspace Technique Applied to Volatile Chemicals Analysis in Dirty Wastewater Streams", Advances in Instrumentation and Control, Instrument Society of America, Research Triangle Park, US, vol. 51, No. Part 1, pp. 119–130, 1996, XP000640488.

Chemical Engineering Progress, "How Do New Process Analyzers Measure Up?", Podkulski, Daniel E., Chevron Products Co., pp. 33–46 (Oct. 1997).

Environmental Science & Technology, "Volatilization of Chemicals From Tap Water to Indoor Air From Contaminated Water Used for Showering", Moya, Jacqueline, Howard–Reed, Cynthia and Corsi, Richard L., vol. 33, No. 14, pp. 2321–2327 (1999).

Application Note, "Use of a GC Analyzer With Continuous Sparger for Monitoring Polar and Nonpolar Species", Driscoll, John N., pp. 16 and 18 (Dec. 1998).

* cited by examiner

HEADSPACE SAMPLING AND MONITORING SYSTEMS AND METHODS

BACKGROUND OF THE INVENTION

The invention relates to sampling and monitoring systems. In particular, the invention relates to headspace sampling and monitoring systems and methods.

A sampling system is typically used to monitor manufacturing processes, in which the sampling system may include analyzing capabilities. The sampling system should obtain a representative sample with minimal operations and time. While such sampling systems have been used in industry, these sampling systems may experience analytical problems, some of which may be attributed to sampling system features and mechanics.

Manufacturing processes may produce by-products, which need monitoring, such as by sampling and analyzing. A manufacturing process may produce volatile organic compound (VOCs) by-products and volatile silicone oils at a process discharge, such as, but not limited to, an aqueous discharge. Typically, VOCs can comprise mixtures of polar and non-polar hydrocarbons. VOCs can pose analytical problems for conventional monitoring and sampling systems. Polar and non-polar hydrocarbons generally require two different and distinct processes for sampling from an aqueous discharge. Non-polar VOCs, such as, but not limited to, benzene, toluene, and aliphatic hydrocarbons including hexane, are generally sampled with a purge-and-trap method. However, polar VOCs, including but not limited to acetone, methanol, and other alcohols, are typically sampled by sparging or dynamic headspace sampling. Alternatively, polar VOCs can be sampled by direct injection gas chromatography (gc).

Various sampling and monitoring systems are known in the art. These systems include on-line systems in which sampling and monitoring is conducted in the "normal" course of manufacturing processes. For example, a representative portion of some wastewater may be directed to a sampling and monitoring system for analyzing that often conducted by purge-and-trap gas chromatography (gc) systems and techniques. While an on-line system has several advantages, it is not always possible to access the wastewater in a manufacturing process. Further, the wastewater that is to be sampled and monitored may not be wastewater that is capable of being sampled on-line. For example, the wastewater may be only accessible after processing is complete, in which the wastewater is collected manually for monitoring.

The manual collection of wastewater can present several problems for sampling and monitoring. These problems include relatively high costs for collecting samples needed for the sampling and monitoring. Further, given the manual aspect of the collecting of samples for monitoring, sediment and other particulate matter may be captured in the sample. Sediments and other particulate matter are undesirable in most monitoring systems. Conduits in conventional sampling systems may be configured too narrowly and be constricted so that fouling and blockage by sediments or particulates often occurs and interrupts monitoring. Thus, filtering of influent aqueous discharge is needed. The filters in monitoring systems need to be cleaned and replaced, which is both inefficient and un-economical.

Therefore, a need exists for a headspace sampling system that can adequately and accurately monitor and sparge wastewater samples. Further, a need exists for a headspace sampling system that can provide precise and reproducible data. Furthermore, a need exists for a headspace sampling system that avoids problems with particulates and sediments in manually collected wastewater.

SUMMARY OF THE INVENTION

A headspace sampling system monitors materials in wastewater is provided in an aspect of the invention. The headspace sampling system comprises a sample receptacle that can contain a wastewater sample; a sparger chamber vapor column; a sample receptacle cover assembly that connects the sparger chamber vapor column to the sample receptacle; a sparger tube; at least one sensing device; and at least one analytic device. The sparger tube and the sample receptacle define a headspace. The sparger chamber vapor column is in communication with the sample receptacle and is closed by a sparger chamber vapor column cover at a second end that is opposed to the sample receptacle. The sparger tube extends into the sample receptacle and the wastewater sample in the sample receptacle. The sparger tube is connected to a source of inert gas at a first end opposed to the sample receptacle and comprises a dispersion device at an end opposed to the first end. The sensing device is disposed in the headspace sampling system in the headspace. The analytic device in communication with the at least one sensing device. Inert gas can flow through the sparger tube into the wastewater sample to separate materials from the wastewater, the sparged materials entering the headspace of the headspace sampling system. The sparged materials are sensed by the sensing device thus providing material signal characteristics, which can be analyzed by the analytic device to determine characteristics of the material from the material signal characteristics and provide information about the characteristics of the material.

Another aspect of the invention provides a method for monitoring materials in wastewater. The method comprising steps of providing a wastewater sample in receptacle, in which the wastewater sample is to be monitored; providing a sparger chamber vapor column; disposing the receptacle and sparger chamber vapor column in fluid cooperation so as to define a headspace in the receptacle and sparger chamber vapor column; providing a sparger tube extending into the receptacle and the wastewater sample therein, the sparger tube comprising a dispersion device to expel air into the wastewater sample; providing a flow of inert gas to the dispersion device to separate materials from the wastewater sample into the headspace; sensing the separated materials; and analyzing the separated materials to provide information about the characteristics of the material.

A further aspect of the invention sets forth a headspace sampling system for separating materials from wastewater, for monitoring the materials separated from the wastewater, analyzing the materials, and communicating results of the analyzing. The headspace sampling system comprises a sample receptacle that can contain a wastewater sample that is to be monitored; a sparger chamber vapor column; a sample receptacle cover assembly comprising a sample receptacle cover and a mounting ring, the sample receptacle cover assembly connects the sparger chamber vapor column to the sample receptacle, the sparger tube and the sample receptacle defining a headspace, the sparger chamber vapor column being in communication with the sample receptacle at a first sparger chamber vapor column end and being closed by a sparger chamber vapor column cover at a second end opposed to the sample receptacle; a sparger tube that extends into the sample receptacle and the wastewater sample in the sample receptacle, the sparger tube being connected to a source of inert gas at a first end opposed to the sample receptacle, sparger tube comprising a dispersion device at an end opposed to the first end; at least one sensing device disposed in the headspace sampling system in the headspace; at least one analytic device in communication with the at least one sensing device; and communications links that can communicate information about the characteristics of the material. The inert gas can flow through the sparger tube into the wastewater sample to separate materials from the wastewater. The materials enter the headspace of the headspace sampling system, and can be sensed by the at least one sensing device. The at least one sensing device provides material signal characteristics, which can be analyzed by the analytic device to determine characteristics of the material from the material signal characteristics and provide information about the characteristics of the material.

These and other aspects, advantages and salient features of the invention will become apparent from the following detailed description, which, when taken in conjunction with the annexed drawings, where like parts are designated by like reference characters throughout the drawings, disclose embodiments of the invention.

DETAILED DESCRIPTION OF THE INVENTION

Figure 1:
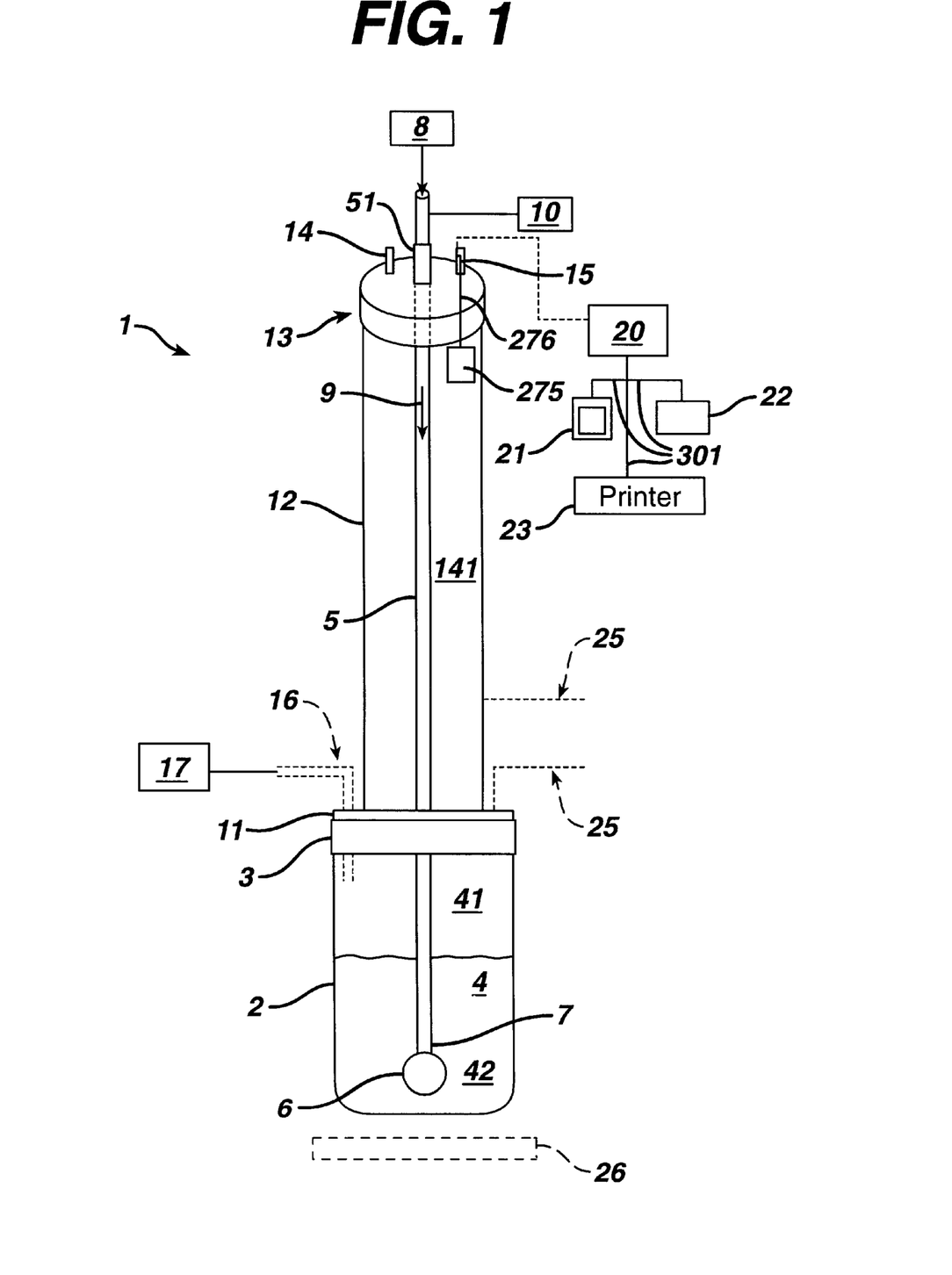
FIG. 1 is a schematic part-sectional illustration of an exemplary headspace sampling and monitoring system, as embodied by the invention.

A headspace sampling and monitoring system 1, as embodied by the invention, can quickly and accurately determine concentrations of analyte materials, such as, but not limited to, volatile organic compounds, including non-polar and polar VOCs (hereinafter collectively referred to as "VOCs"), toluene, xylenes, methyl chloride, and volatile silicone oils, in waste water samples. The description of the invention will refer to the materials as VOCs in the wastewater, however, this description is merely exemplary of materials to be separated from the wastewater, and is not intended to limit the invention in any manner.

The headspace sampling and monitoring system 1 (hereinafter "headspace sampling system") comprises at least a device for sparging samples of static wastewater, in which the term "static" means that the wastewater is not flowing, as compared to flowing wastewater that is often encountered in a manufacturing system or environment. The sparging can separate VOCs from the wastewater, so the VOCs can be detected by a sensing system of the headspace sampling system 1.

The headspace sampling system 1 can further comprise a sensing system and analytic system for analyzing and evaluating sparged wastewater. The sensing system, which analyzes and evaluates, can also provide sparged analyzed and evaluated information (hereinafter "sparged information") to at least one user. The sparged information can be provided by appropriate communication links, as described below.

The headspace sampling system 1, as embodied by the invention, comprises a sample receptacle 2. The sample receptacle 2 can comprise any appropriately formed receptacle that can cooperate with the features of the headspace sampling system 1, as described hereinafter. For example, and not intending to limit the invention, the sample receptacle 2 can comprise a receptacle that is formed from a non-reactive and non-sorbent material, such as but not limited to at least one of glass and polyvinyl chloride (PVC). These materials are merely exemplary of non-reactive and non-sorbent materials within the scope of the invention.

The sample receptacle 2 is closed by a sample receptacle cover assembly that comprises a sample receptacle cover 3 and a mounting ring 11. The sample receptacle cover 3 can define a sample receptacle interior 4 within the sample receptacle 2. The sample receptacle cover 3 can be connected to the sample receptacle 2 by any appropriate connection, for example, but not limited to, screw threads, bayonet couplings, friction fits, and combinations thereof. A wastewater sample 42 is disposed in the sample receptacle 2. For example, as discussed above, the wastewater sample 42 can be provided in the sample receptacle 2 by manual collection. Although the headspace sampling system 1 is described herein with respect to static collected wastewater samples 42, this description is merely for illustrative purposes. The headspace sampling system 1 is adapted for use with other sampling and monitoring systems, such as, but not limited to, automated sample collection systems.

The headspace sampling system 1 comprises a sparger tube 5 that extends into the interior of the sample receptacle 2 and into the wastewater sample 42 contained therein. The sparger tube 5 can be formed of sturdy non-reactive materials, such as, but not limited to, stainless steel. An end 7 of the sparger tube 5 comprises a dispersion device 6. The dispersion device 6 can comprise a porous member through which gas for sparging and separating (often referred to as "partitioning") the VOCs can readily pass, for example a spherical porous, fused aluminum oxide diffuser. Other exemplary materials for the dispersion device 6 comprise, but are not limited to, porous stone, sintered metal, and other such materials. The dispersion device 6 comprises a structure that is not readily clogged by at least one of particulate and sediments in the wastewater. Further, dispersion device 6 comprises a device onto which particulate and sediments in the wastewater do not tend to accumulate. Thus, the headspace sampling system 1 does not require the time consuming and costly endeavor of wastewater sample conditioning that is normally required by conventional sampling and monitoring systems to remove particulates and sediments.

The other end 55 of the sparger tube 5 is connected to a source of inert gas 8, for example but not limited to, filtered air. The sparger tube 5 comprises a passage therein so that a stream 9 of inert gas from the source of inert gas 8 can flow down the sparger tube 5 to the dispersion device 6. The inert gas will exit the dispersion device 6, enter the wastewater sample 42, and separate VOCs and other such materials from the wastewater sample 42 into a headspace 41 in the sample receptacle 2. The flow and rate of flow stream 9 of inert gas can be controlled by a flow control device, such as, but not limited to, a flow control meter 10 that is in communication with the sparger tube 5. Thus, a flow meter 10 can control the flow of the stream 9 of inert gas and also provide a flow rate of the inert gas that enhances separating VOCs from the wastewater sample 42.

The headspace 41 can communicate with a headspace extension 141 that is located in a sparger chamber vapor column 12. The sparger chamber vapor column 12 (hereinafter "sparger column") comprises a generally cylindrical tubular element that is connected to the sample receptacle cover 3 on the sample receptacle 2. A mounting ring 11 of the sample receptacle cover assembly can be used to connect the sparger column 12 to the sample receptacle cover 3 and the sample receptacle 2. The sample receptacle cover 3 comprises at least one passage therethrough, so separated VOCs from the waste water sample 42 can communicate with and flow into the headspace extension 141 in the sparger column 12.

The sparger column 12 is closed at an end opposed to its connection to the sample receptacle cover 3. A sparger column cover 13 is disposed on the sparger column 12 that can sealingly engage the sparger column 12. Thus, any separated VOCs in the sparger column 12 will not escape to the ambient atmosphere. The sparger column cover 13 comprises at least one fitting or port (hereinafter "port") and can comprise a plurality of ports. The sparger column cover 13 comprises a sparger tube port 51 through which the sparger tube 5 can extend into the system 1. The sparger column cover 13 can further comprise an exhaust port 14 so that pressure in the sparger column 12 can be vented or exhausted. The exhaust port 14 may be vented, connected to an exhaust treatment system, or connected to a condensing system, if desired.

The sparger column cover 13 may also comprise a sensor port 15 for the sensing system. The sensor port 15 permits a sensor lead 276 to extend from a sensing device 275. The sensing device 275 can comprise, but is not limited to, at least one of a robust metal-oxide semiconductor (MOS) sensor and micro-gas chromatography (micro-gc) unit, to pass therethrough and connected with analytic devices (as discussed hereinafter). The term "robust" means that long-term performance occurs with little or no upkeep or maintenance and is not prone to failure. The following description of the invention will refer to a MOS sensor, however, this description is merely exemplary, and is not intended to limit the invention in any manner. Sensor (275) resides in sparger column, connected through sensor port 15.

Figure 2:
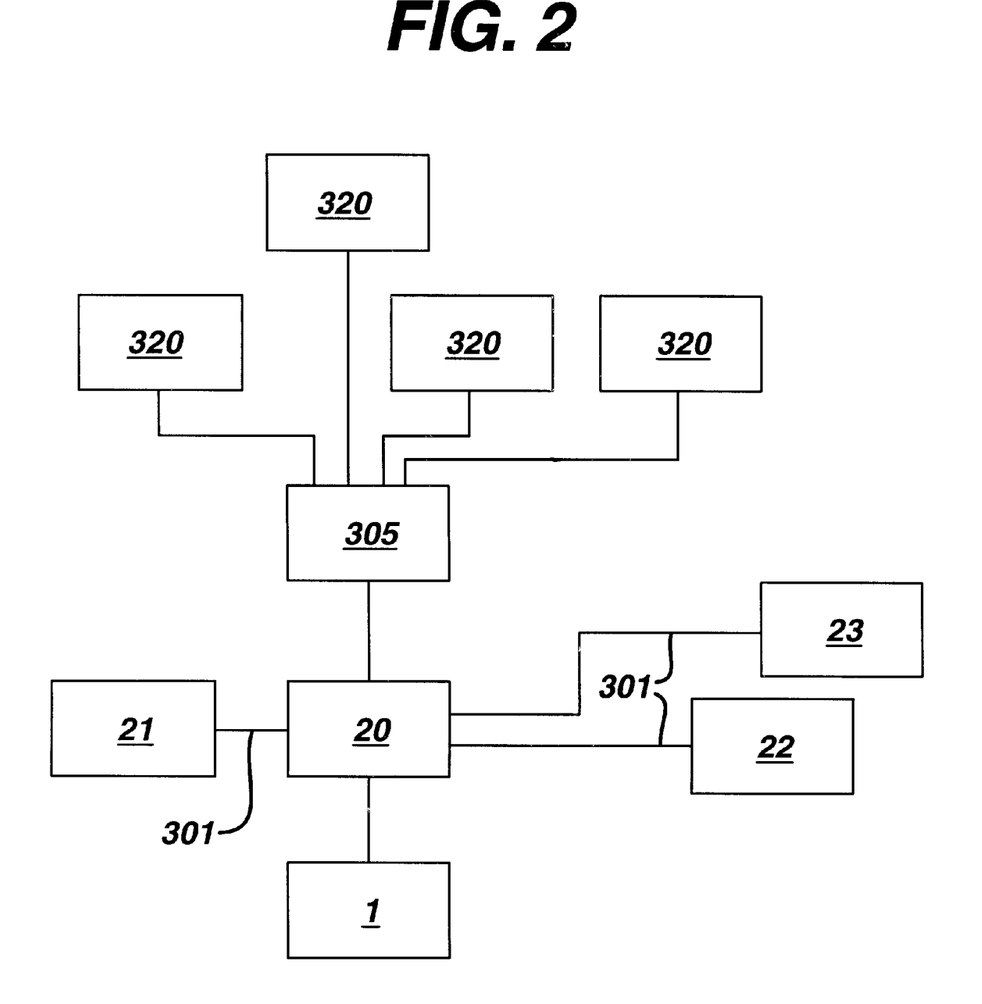
FIG. 2 is a schematic a block diagram of a headspace sampling and monitoring system, as embodied by the invention, connected to analytic and communication devices.

The lead 276 from the sensing device 275 can be connected by communication links 301 to an appropriate analytic device 20, and if desired a display 21 and printer 23. The analytic device 20 can be selected from a variety of available process analyzers. A MOS sensor when in communication with the headspace 41 and 141 and connected to the analytic device 20, can provide real-time and near real-time monitoring and analyzing. The term "real-time" is used with its accepted meaning in the art, and means that any delays from the time the process variable information is monitored, evaluated and analyzed, and then made available to the machine operator is minimal, for example on the order of minutes, and possibly a few seconds, or even longer if the need for the information is defined as such and the data may still be relevant and of value to the interested party, if any delay is present. Also, the term "real-time" can mean a time required by a headspace sampling system 1 user to obtain data.

The headspace sampling system 1 can be connected by communication links 301 to provide data to authorized parties or users of the headspace sampling system 1. For example, FIG. 2 illustrates a block diagram of the headspace sampling system 1 static headspace sampling and monitoring system 1. Further, the sparged information from the analytic device 20 can be transferred directly to a party, for example by communication link 301. Alternatively, the sparged information from the analytic device 20 can be transferred directly to a party, for example by communication links 301 that lead to a common data gathering location 305, such as, but not limited to, a web page. The communication links 301 include, but are not limited to include, but are not limited to, at least one of a phone modem, network connection, communication, radio communication and other wireless communication systems, cellular communication, satellite communication, web access communication, Internet access communication, and Intranet access communication, and combinations thereof.

The use of a web page with the headspace sampling system 1 provides real-time monitoring and analysis data to parties 320 who can readily benefit from the information. In the past, evaluations occurred randomly, irregularly, and may not normally be transmitted in an expedited manner. With the headspace sampling system 1, as embodied by the invention, parties that are actually located at the headspace sampling system 1 can quickly obtain analyzed and evaluated information, which is provided in a form that is valuable and easy to use. Also, other parties 320 that may not be located at the headspace sampling system 1, for example but not limited to regulatory agencies, can also obtain monitored data in real-time, so as to avoid undesirable time delays. With the real-time monitored data, a party 320 may take immediate steps in response to the data. Also, with the real-time monitored data via communication links, feedback from a party can be provided and received via the communication links.

The headspace sampling system 1, as embodied by the invention, enhances robustness of sampling and monitoring systems, as the maintenance typically associated with such systems for conditioning sediments and cleaning of the dispersion device is reduced. The non-reactive and non-sorbent materials discussed above are merely exemplary. Although, PVC and stainless steel are disclosed, other non-reactive and non-sorbent materials are within the scope of the invention.

In operation, a static wastewater sample 42 is collected in the sample receptacle 2, for example by a manual collection process. The wastewater sample 42 and the sample receptacle 2 are placed in cooperation with the other features of the headspace sampling system 1. For example, the other features of the headspace sampling system 1, including but not limited to the sparger chamber vapor column 12, the sample receptacle cover 3, the mounting ring 11, the sparger chamber cover 13, and the features associated with the headspace sampling system 1 through the sparger chamber cover 13, can be desk or bench mounted. These features of the headspace sampling system 1, as embodied by the invention, can be attached to a ring stand, wall, or other support (not illustrated) for the desk or bench operation. Thus, wastewater samples can be easily placed into the headspace sampling system 1.

Once the sample receptacle 2 is connected to the other features of the headspace sampling system 1, air can be passed through the sparger tube 5 and dispersion device 6 and enter the wastewater sample 42. The air separates VOCs from the wastewater sample 42, and the VOCs enter the headspace 41 and the head space extension 141. The sensing device 275 can then detect VOCs in this headspace. VOCs can then be analyzed by the associated analytic device 20 that can determine a VOC type from the VOC signal characteristics. Further, the VOC type determined by the analytic device 20 can be communicated over the communications link 301, if desired.

Once one wastewater sample 42 has been analyzed and the analyzing process is complete, the wastewater sample 42 can be removed from the headspace sampling system 1.

VOC signals from the sensing device, for example a MOS sensor, will return to a zero signal, which indicates absence of VOCs. If desired, a second wastewater sample may be provided to the headspace sampling system 1, for analyzing.

Figure 3:
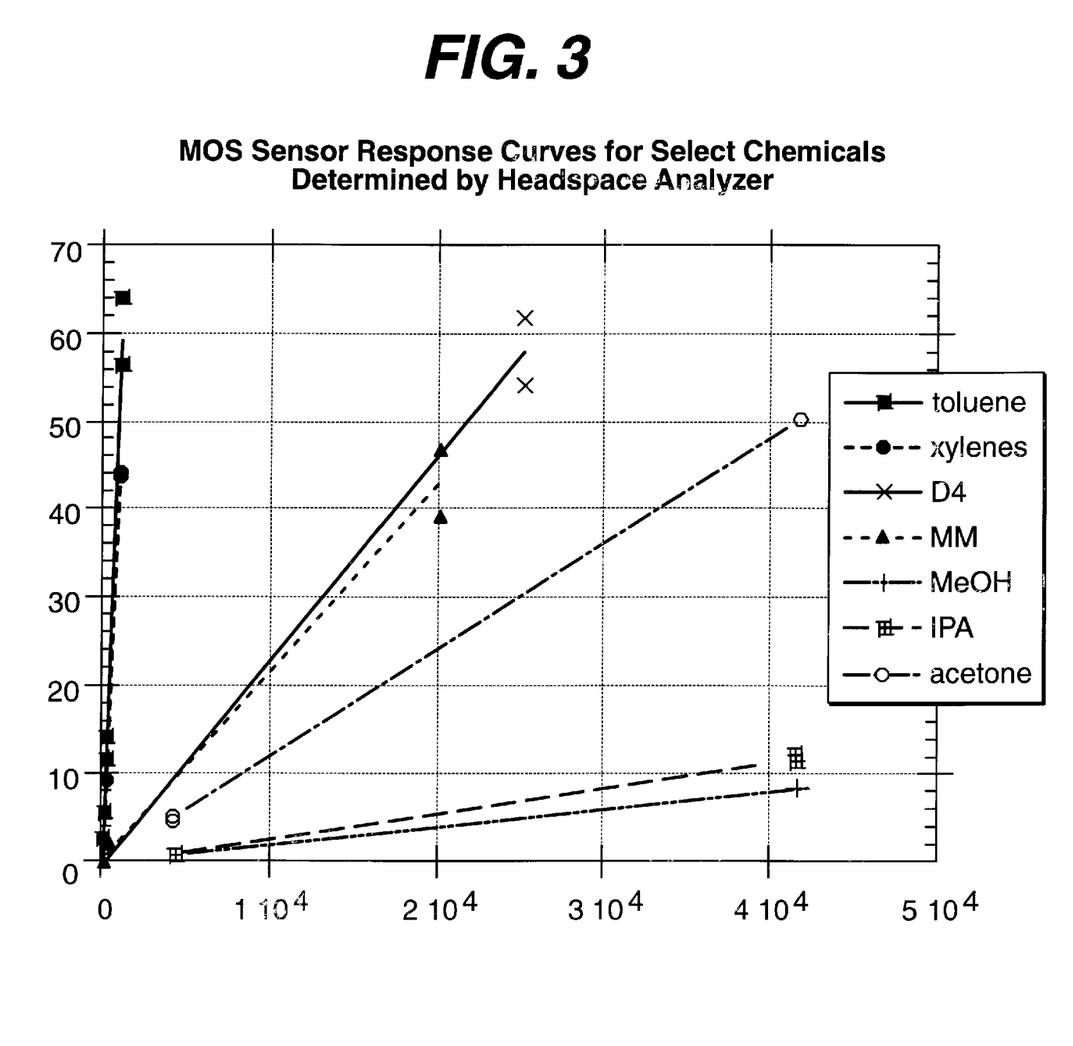
FIG. 3 is a graph of response curves for various materials measured by an exemplary headspace sampling and monitoring system, as embodied by the invention, illustrating signal versus aqueous concentration.

Table 1 (below) and FIG. 3 provide exemplary data obtained from the headspace sampling system 1 during analyzing processes for various analytes. As is evidenced from Table 1, initial response time is short, thus the headspace sampling system 1 can provide expedited monitoring and analysis of the wastewater samples. The analyzed data from the analytic device 20 can be compared with response or calibration curves (FIG. 3), which may have been created by measuring know concentrations of VOCs. The comparison may provide indications of a nature of chemicals that are present in the wastewater sample. The analytic device 20 of the headspace sampling system 1 can be loaded with and calibrated for known VOC concentrations under conditions for future analyses. Thus, the analytic device 20 can provide future monitoring sampling operations for the headspace sampling system 1.

Response of MOS Sensor* in Benchtop Vapor Sampler to Select Chemicals

| chemical | conc. (ppb) | max. signal | time to initial response | time to max. response |
| --- | --- | --- | --- | --- |
| toluene | 57 | 2.7 | <5 sec. | ~1 min |
|  | 114 | 5.8 | <5 sec. | ~1 min |
|  | 228 | 13.0 | <5 sec. | ~1 min |
|  | 1142 | 59.0 | <5 sec. | ~1 min |
| xylenes | 114 | 6.0 | <5 sec. | ~1 min |
|  | 227 | 10.4 | <5 sec. | ~1 min |
|  | 1136 | 44.0 | <5 sec. | ~1 min |
| D4 | 505 | 3.4 | <5 sec. | ~1 min |
|  | 2525 | 5.1 | <5 sec. | ~1 min |
|  | 25,250 | 57.8 | <5 sec. | ~1 min |
| SF 9600 | 101,000 | 0.1 | — | — |
| MM | 202 | 0.2 | <5 sec. | ~1 min |
|  | 404 | 2.2 | <5 sec. | ~1 min |
|  | 20,180 | 42.9 | <5 sec. | ~1 min |
| MeOH | 4179 | 0.8 | <10 sec. | ~2 min |
|  | 41,792 | 8.3 | <10 sec. | ~2 min |
| IPA | 4150 | 0.7 | <10 sec. | ~2 min |
|  | 41,475 | 11.6 | <10 sec. | ~2 min |
| acetone | 4180 | 5.0 | <10 sec. | ~2 min |
|  | 41,800 | 50.2 | <10 sec. | ~2 min |

Calibration range: 0–100 ppmv

The headspace sampling system 1 may additionally comprise an air influent tube 25 to dilute the VOCs that have been separated from the wastewater sample by the headspace sampling system 1. The air influent tube 25 can be connected to at least one of the headspace 41 and headspace extension 141, for example by passing through the cover 3 and a wall of the sparger chamber vapor column 12, respectively. The air influent tube 25 is illustrated in dashed lines in FIG. 1 in both positions. The air influent tube 25 can add air, for example, but not limited to, filtered air to the headspace 41 or the headspace extension 141 if concentrations of separated VOCs exceed sensing limits of the MOS sensor.

Further, the headspace sampling system 1 may also include a heater system for heating the wastewater in the sample receptacle 2. The heater system 26 is illustrated in phantom in FIG. 1 and can comprise any heater device that can apply heat to the wastewater sample 42. The heat can to facilitate the separating of VOCs from the wastewater sample 42 into the headspace of the headspace sampling system 1.

The headspace sampling system 1 provides sampling of both non-polar and polar VOCs together without separate monitoring setups. Further, the headspace sampling system 1 can be configured for real-time monitoring and can be coupled to continuous or automated process analyzers. Thus, the headspace sampling system 1 can provide real-time data for process control and feedback, without time delays experienced by conventional sampling and monitoring systems.

While various embodiments are described herein, it will be appreciated from the specification that various combinations of elements, variations or improvements therein may be made by those skilled in the art, and are within the scope of the invention.

We claim:

1. A headspace sampling system for monitoring materials in wastewater, the headspace sampling system comprising:
   a sample receptacle that can contain a wastewater sample that is to be monitored;
   a sparger chamber vapor column;
   a sample receptacle cover assembly comprising a sample receptacle cover and a mounting ring, the sample receptacle cover assembly connecting the sparger chamber vapor column to the sample receptacle, the sparger tube and the sample receptacle defining a headspace, the sparger chamber vapor column being in communication with the sample receptacle at a first sparger chamber vapor column end and being closed by a sparger chamber vapor column cover at a second end opposed to the sample receptacle;
   a sparger tube that extends into the sample receptacle and the wastewater sample in the sample receptacle, the sparger tube being connected to a source of inert gas at a first end opposed to the sample receptacle, the sparger tube comprising a dispersion device at an end opposed to the first end;
   at least one sensing device disposed in the headspace; and
   at least one analytic device in communication with the at least one sensing device;
   wherein inert gas can flow through the sparger tube into the wastewater sample to separate materials from the wastewater, the sparged materials entering the headspace of the headspace sampling system, the sparged materials being sensed by the at least one sensing device, the at least one sensing device providing material signal characteristics, and the material signal characteristics can be analyzed by the analytic device to determine the material type from the material signal characteristics.

2. A system according to claim 1, wherein the system comprises a part of a network of a monitoring system.

3. A system according to claim 1, the headspace sampling system further comprising a heater device, wherein the heater device can apply heat to the wastewater sample in the sample receptacle, and the heat can facilitate separating of materials from the wastewater sample into the headspace of the headspace sampling system.

4. A system according to claim 1, the headspace sampling system further comprising an air influent tube connected to the headspace to dilute materials that have been separated from the wastewater sample.

5. A system according to claim 1, wherein the sparger tube is comprised of stainless steel.

6. A system according to claim 1, wherein the dispersion device comprises a porous member through which gas for sparging can pass.

7. A system according to claim 6, wherein the dispersion device comprises at least one of a fused aluminum oxide diffuser, a porous stone diffuser, and a sintered metal diffuser.

8. A system according to claim 1, wherein at least one of the sample receptacle, sparger chamber vapor column, and a sample receptacle cover assembly comprises polyvinyl chloride.

9. A system according to claim 1, wherein the sparger chamber vapor column cover is disposed on the sparger chamber vapor column to sealingly engage the sparger chamber vapor column to prevent escape of materials.

10. A system according to claim 1, wherein the sparger chamber vapor column cover comprises at least one of a sparger tube port through which the sparger tube can extend, and an exhaust port that can vent the headspace.

11. A system according to claim 10, wherein the exhaust port may vent the headspace to at least one of an exhaust treatment system and a condensing system.

12. A system according to claim 10, wherein the sparger chamber vapor column cover comprises a sensor port for the sensing system.

13. A system according to claim 12, wherein the at least one sensing device comprises at least one of a metal-oxide semiconductor (MOS) sensor and a micro-gas chromatography (micro-gc) sensor unit.

14. A system according to claim 1, wherein the sensor port permits a sensor lead to extend from the at least one sensing device to the at least one analytic device.

15. A system according to claim 1, the headspace sampling system further comprises a flow control meter that can control the flow of the inert gas in the sparger tube, the flow control meter also being able to control a flow rate of the inert gas to the wastewater sample.

16. A method for separating from wastewater and monitoring a material separated from the wastewater, the method comprising:

proving wastewater sample in receptacle, in which the wastewater sample is to be monitored;

providing a sparger chamber vapor column;

disposing the receptacle and sparger chamber vapor column in fluid cooperation so as to define a headspace in the receptacle and sparger chamber vapor column;

providing a sparger tube extending into the receptacle and the wastewater sample therein, the sparger tube comprising a dispersion device to expel an inert gas into the wastewater sample;

providing a flow of the inert gas to the dispersion device for separating a material from the wastewater sample into the headspace;

sensing a separated material; and analyzing separated materials to provide information about the material.

17. A method according to claim 16, the method further comprising communicating information about the material.

18. A method according to claim 17, wherein the step of communicating comprises communicating the information via a monitor.

19. A method according to claim 17, wherein the step of communicating comprises communicating the information via a printer.

20. A method according to claim 17, wherein the step of communicating comprises communicating the information via a network.

21. A method according to claim 17, wherein the step of communicating comprises communicating the information via a communication link selected from at least one of: a phone modem, network connection, radio communication and other wireless communication systems, cellular communication, satellite communication, web access communication, Internet access communication, and Intranet access communication, and combinations thereof.

22. A method according to claim 16, the method further comprising a step of applying heat to the wastewater sample to facilitate separating of the material from the wastewater.

23. A method according to claim 16, the method further comprising a step of adding air to the headspace to dilute the material.

24. A method according to claim 16, the method further comprising a step of selecting the dispersion device from at least one of: a fused aluminum oxide diffuser, a porous stone diffuser, and a sintered metal diffuser.

25. A method according to claim 16, the method further comprising a step of sealing the sparger column to prevent escape of the material.

26. A method according to claim 16, the method further comprising a step of providing at least one of: a sparger tube port, through which the sparger tube can extend, and an exhaust port that can vent the headspace.

27. A method according to claim 26, the method further comprising a step of venting the headspace to at least one of an exhaust treatment system and a condensing system.

28. A method according to claim 16, wherein the step of sensing comprises providing a sensing device, the sensing device communicating with the headspace by a sensor port.

29. A method according to claim 28, wherein the step of analyzing comprises providing an analytic device, wherein the sensor port permits a sensor lead to extend from the sensing device to the analytic device.

30. A method according to claim 28, wherein the sensing device comprises at least one of a metal-oxide semiconductor (MOS) sensor and a micro-gas chromatography (micro-gc) sensor unit.

31. A method according to claim 16, the method further comprising at least one of a step of controlling a flow of gas and a step of controlling a flow rate of gas.

32. A headspace sampling system for separating materials from wastewater, for monitoring the materials separated from the wastewater, analyzing the materials, and communicating results of the analyzing, the headspace sampling system comprising:

a sample receptacle that can contain a wastewater sample that is to be monitored;

a sparger chamber vapor column;

a sample receptacle cover assembly comprising a sample receptacle cover and a mounting ring, the sample receptacle cover assembly connecting the sparger chamber vapor column to the sample receptacle, the sparger tube and the sample receptacle defining a headspace, the sparger chamber vapor column being in communication with the sample receptacle at a first sparger chamber vapor column end and being closed by a sparger chamber vapor column cover at a second end opposed to the sample receptacle;

a sparger tube that extends into the sample receptacle and the wastewater sample in the sample receptacle, the sparger tube being connected to a source of inert gas at a first end opposed to the sample receptacle, the sparger tube comprising a dispersion device at an end opposed to the first end;

at least one sensing device disposed in the headspace;

at least one analytic device in communication with the at least one sensing device; and communications links that can communicate information about the characteristics of the material;

wherein inert gas can flow through the sparger tube into the wastewater sample to separate materials from the wastewater, the sparged materials entering the headspace of the headspace sampling system, the sparged materials being sensed by the at least one sensing device, the at least one sensing device providing material signal characteristics, and the material signal characteristics can be analyzed by the analytic device to determine characteristics of the material from the material signal characteristics and provide information about the characteristics of the material.

33. A system according to claim 32, wherein the communications links can be connected to at least one at least one of a monitor, a network, and a printer.

34. A system according to claim 32, wherein the communications links comprise at least one of: a phone modem, network connection, radio communication and other wireless communication systems, cellular communication, satellite communication, web access communication, Internet access communication, and Intranet access communication, and combinations thereof.

35. A system according to claim 26, wherein the headspace sampling system further comprises a heater device, the heater device can apply heat to the wastewater sample in the sample receptacle, and the heat can facilitate separating of materials from the wastewater.

36. A system according to claim 32, wherein the headspace sampling system further comprises an air influent tube connected to the headspace to dilute materials that have been separated from the wastewater.

37. A system according to claim 32, wherein the dispersion device comprises at least one of a fused aluminum oxide diffuser, a porous stone diffuser, and a sintered metal diffuser.

38. A system according to claim 32, wherein the sparger column cover is disposed on the sparger column and sealingly engages the sparger column to prevent escape of materials.

39. A system according to claim 32, therein the sparger column cover comprises a sparger tube port through which the sparger tube can extend, an exhaust port that can vent the headspace, and a sensor port for the sensing device.

40. A system according to claim 39, wherein the sensor port permits a sensor lead to extend from the at least one sensing device to the at least one analytic device.

41. A system according to claim 32, wherein the sensing device comprises at least one of a metal-oxide semiconductor (MOS) sensor and a micro-gas chromatography (micro-gc) sensor unit.

* * * * *